US007986992B2

(12) United States Patent
Ideker et al.

(10) Patent No.: US 7,986,992 B2
(45) Date of Patent: Jul. 26, 2011

(54) APPARATUS AND METHOD FOR TREATING ATRIAL FIBRILLATION AND ATRIAL TACHYCARDIA

(75) Inventors: Raymond E. Ideker, Birmingham, AL (US); Derek J. Dosdall, Birmingham, AL (US); James P. Ruse, Clermont, FL (US); Greg Ruse, legal, Clermont, FL (US); Richard B. Ruse, Atlanta, GA (US); Scott J. Bohanan, Duluth, GA (US)

(73) Assignees: Ruse Technologies, LLC, Atlanta, GA (US); The UAB Research Foundation, Birmingham, AL (US)

( * ) Notice: Subject to any disclaimer, the term of this patent is extended or adjusted under 35 U.S.C. 154(b) by 500 days.

(21) Appl. No.: 12/272,275

(22) Filed: Nov. 17, 2008

(65) Prior Publication Data

US 2009/0157130 A1 Jun. 18, 2009

Related U.S. Application Data

(60) Provisional application No. 60/988,553, filed on Nov. 16, 2007.

(51) Int. Cl.
*A61N 1/00* (2006.01)
(52) U.S. Cl. .......................................................... 607/5
(58) Field of Classification Search .................. 607/4, 5, 607/6, 9, 14, 15
See application file for complete search history.

(56) References Cited

U.S. PATENT DOCUMENTS

| 6,430,449 | B1 * | 8/2002 | Hsu et al. ...................... 607/126 |
| 6,766,195 | B1 * | 7/2004 | Bornzin et al. ................. 607/14 |
| 7,389,140 | B1 | 6/2008 | Kroll |
| 7,555,341 | B2 | 6/2009 | Moffitt et al. |
| 7,647,115 | B2 | 1/2010 | Levin et al. |
| 7,657,310 | B2 | 2/2010 | Buras |
| 2003/0045909 | A1 | 3/2003 | Gross et al. |
| 2005/0065553 | A1 | 3/2005 | Ben Ezra et al. |
| 2005/0131475 | A1 | 6/2005 | Smits |
| 2006/0074450 | A1 | 4/2006 | Boveja et al. |
| 2006/0116736 | A1 | 6/2006 | DiLorenzo |
| 2008/0103440 | A1 | 5/2008 | Ferren et al. |

OTHER PUBLICATIONS

USPTO Office Action dated Sep. 8, 2010 issued in U.S. Appl. No. 12/393,899.
USPTO Office Action dated Oct. 19, 2010 issued in U.S. Appl. No. 12/272,296.

* cited by examiner

*Primary Examiner* — George Manuel
*Assistant Examiner* — Robert Wieland
(74) *Attorney, Agent, or Firm* — William H. Dippert; Eckert Seamans Cherin & Mellott, LLC

(57) ABSTRACT

An apparatus for treating atrial fibrillation or atrial tachycardia comprises means for dynamically steering or selecting two or more current vector paths sequentially or simultaneously for defibrillation to change the transmembrane potential in the left and right atria sufficiently to halt AF or AT. The apparatus is useful to treat AF or AT in patients.

26 Claims, 7 Drawing Sheets

SYSTEM DIAGRAM

SYSTEM DIAGRAM

AMPLIFIER ARRAY

NOTE: DRIVER STAGES FOR AMPLIFIERS ARE OMITTED FOR CLARITY

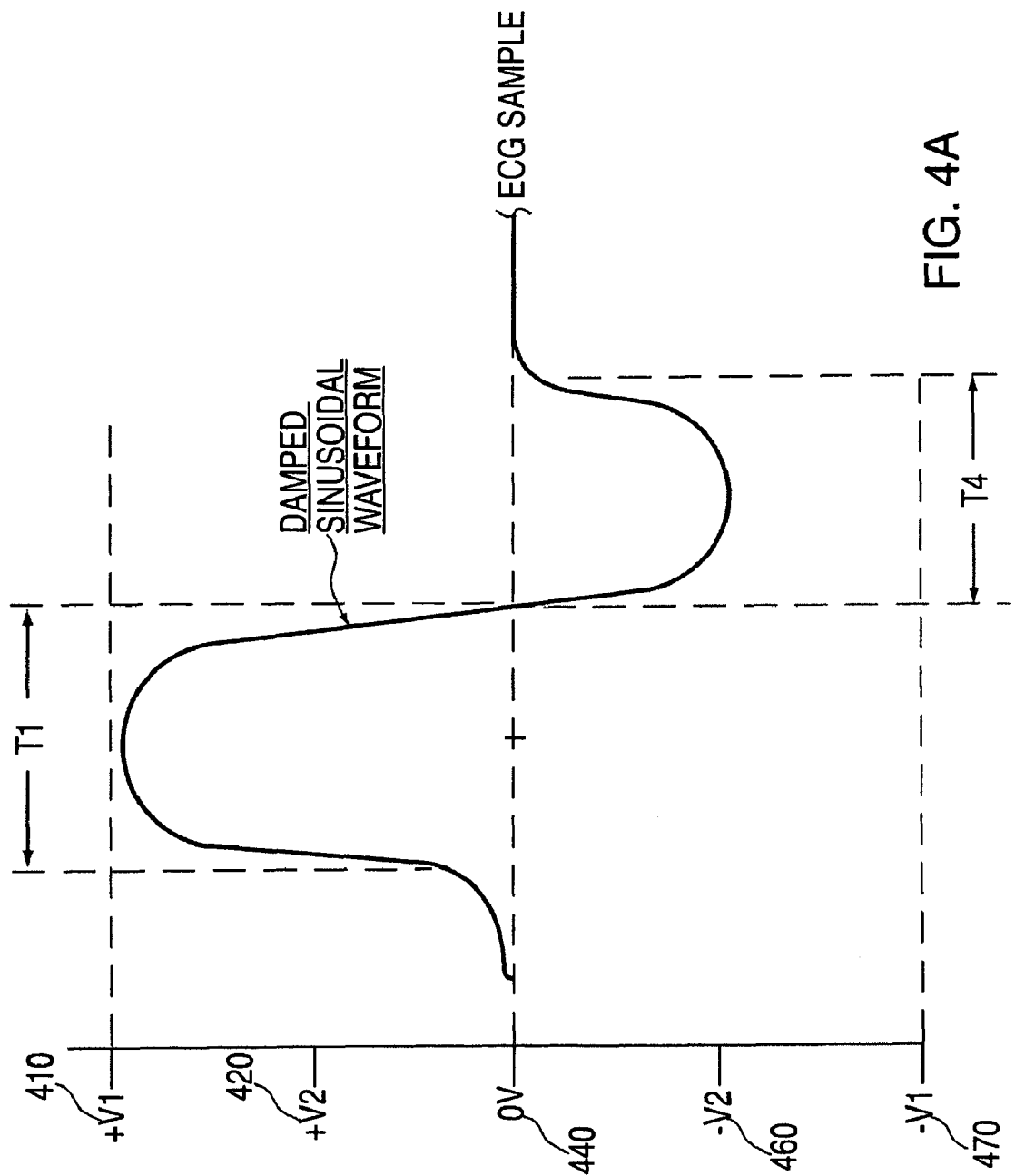

Possible lead wire placement for sequential defibrillation shocks:

RA ⟶ dCS
pCS ⟶ LSV
SVC ⟶ pCS
SVC ⟶ dCS
RAA ⟶ CS
SVC ⟶ RV

Abbreviations:

RA=Right Atria
RV=Right Ventricle
SP=Atrial Septum
pCS=Proximal Coronary Sinus
dCS=Distal Coronary Sinus
SVC=Super Vena Cava
IVC=Inferior Vena Cava
LSV=Left Subclavian Vein
RAA=Right Atrial Appendage.

APPARATUS AND METHOD FOR TREATING ATRIAL FIBRILLATION AND ATRIAL TACHYCARDIA

CROSS-REFERENCE TO RELATED APPLICATION

This application is based upon and corresponds to commonly assigned, U.S. Provisional Patent Application Ser. No. 60/988,553, filed Nov. 16, 2007, incorporated herein by reference in its entirety.

FIELD OF THE INVENTION

This invention relates to the treatment of atrial fibrillation [AF] and atrial tachycardia [AT]. More particularly, this invention relates to a method for treating atrial fibrillation or atrial tachycardia which comprises dynamically steering or selecting two or more current vector paths sequentially or simultaneously for defibrillation to change the transmembrane potential in the left and right atria sufficiently to halt AF or AT.

BACKGROUND OF THE INVENTION

Fast atrial arrhythmias such as AF and AT are abnormal heart rhythms which afflict around three million people each year in the United States. The most prevalent evidence of the disease electrically is a preponderance of irregular AF wavelets of activation that is frequently generated in the pulmonary veins [PVs] and is conducted into the left atrium and then the right atrium causing chaotic and rapid activation that interferes with the normal SA/AV cardiac electrical pathways and causes rapid, irregular ventricular contractions. These atrial tachycardias can be in the form of atrial fibrillation or atrial flutters, typical and atypical, which may vary in terms of severity and rate. AF makes the ventricular response so irregular and fast that it interferes with normal blood flow through the heart chambers, can lead to severe structural heart disease, and can be life-threatening if not treated effectively. While the irregular rate of ventricular contraction during AF and AT may compromise cardiac output and cause fatigue, much of the increased mortality associated with AF is due to clot formation due to the poor circulation in the atria that embolizes to cause stroke, renal infarcts, etc. Persistent AF over weeks or months is particularly dangerous.

There are a number of known modalities for treating atrial tachycardias. The "Maze Procedure" was developed many years ago and effects a cure rate of at least 90% for AF. This procedure involves "cutting" surgical lines or patterns in the right and left atrium [RA and LA] to interrupt unwanted conduction pathways that cause AF. The drawback to this procedure is that it requires open heart surgery and is usually performed on a patient only if there is another more important reason to enter the heart via major surgery, such as a valve replacement or a similar procedure.

RF/microwave ablation, cryo-ablation, ultrasound ablation, or variants of the Cox-Maze procedure are used to burn, freeze, or cut and score lines in the right and left atria. Ablation is performed inside or just outside the PVs and ostia in an attempt to interrupt sources of activation wavefronts that arise in the PVs and propagate into the atria and lead to AF and AT. There are concerns and known side effects such as esophageal fistulae and stenosis of the PV ostia as a result of these ablation procedures. Each case is unique in that there are infinite combinations of tissue conduction pathways and electro-physiologic anomalies and differences within each person that cause the wavelet trains that cause AF and atrial flutter. Knowing where to ablate the tissues of interest is difficult, at best. Also, the cure rate is less than optimum for persons with chronic AF and severe structural heart disease as compared to persons with paroxysmal or occasional/-idiopathic AF/flutter. It is also difficult to make the long ablation lesions continuous and transmural.

Another procedure is DC cardioversion shock therapy to convert AF/flutter to sinus rhythm. This is an excellent conversion tool; however, unless the underlying cause of the AF is resolved, it most likely will recur. Implantable cardioverter defibrillators [ICDs] have been used for conversion of AF, but since the patient is conscious when the shock is delivered, many individuals find the discomfort of the shock intolerable. These systems generally use a "hot can" approach where a very high voltage and current are delivered through the heart and the left chest and pectoral areas, causing significant pain during a defibrillation or cardioversion shock. One advantage of an ICD with AF cardioversion capability is to reduce the amount of time that AF persists before cardioversion to reduce the risk of clot formation.

Anti-arrhythmia drug therapy is effective in many cases even if the AF is not entirely converted back to a normal sinus rhythm. A primary cause for concern is that these drugs are systemic and affect other systems such as the liver, kidneys, and heart, and can also cause fatigue associated with loading and maintenance doses of these drugs.

In patients who do not respond to medications and who are not good candidates for the previous methods for curing or controlling AF, the AV node may be ablated to create complete heart block so that the rapid, irregular atrial activations do not propagate to the ventricles and a pacemaker is implanted to control the heart's rate and rhythm. Drawbacks with the use of pacemakers include possible lead fractures and the abnormal activation sequence they cause in the ventricles, which leads to an abnormal contraction sequence and decreased ventricular function.

Thrombolytic drugs in conjunction with anti-arrhythmic drugs are valuable to prevent thromboembolisms and slow the heart rate. However, long term use of thrombolytic agents may have side effects that can be serious such as hemorrhage.

OBJECTS OF THE INVENTION

It is a primary object of the present invention to provide a method and an ICD for dynamically steering or selecting two or more current vector paths sequentially or simultaneously for defibrillation or cardioversion.

It is another object of the present invention to deliver a biphasic ascending or descending exponential, ramp, or damped sinusoidal waveform which is most efficient with respect to the transmembrane potential response within the myocardium by using an amplifier array where any two, three, or four amplifiers and their respective electrodes may be driven differentially as to draw current through selected current pathways or different angular perspectives.

It is yet another object of the present invention to provide an implantable atrial defibrillation device which uses less energy than conventional defibrillation devices by utilizing sequential or simultaneous shocks at a reduced voltage amplitude thereby reducing pain levels associated with electrical shocks.

It is yet another object of the present invention to provide an implantable defibrillator which defibrillates with higher voltage and current waveforms which minimize tissue stunning and damage.

It is yet another object of the present invention to provide an external defibrillator device which defibrillates with a higher voltage and current using the same circuit topologies and principles as the implantable version.

It is still another object of the present invention to defibrillate using biphasic sequential shocking pulses that are in the range of from about 2.5 ms to about 8 ms positive and negative time periods to minimize energy consumption.

The above and other objects of the present invention will become more readily apparent when reference is made to the following descriptions taken in conjunction with the attached detailed drawings.

SUMMARY OF THE INVENTION

According to the invention, a method and an ICD are provided for dynamically steering or selecting two or more current vector paths sequentially or simultaneously for defibrillation or cardioversion. A primary intent of the invention is to change the transmembrane potential in the left and right atria sufficiently to halt AF or AT with smaller shocks than required using traditional devices which defibrillate through a single current path or using devices that deliver shocks across two or more current pathways but that cannot dynamically alter or steer the voltage and current amplitude through each pathway.

In one aspect of the invention a biphasic ascending or descending exponential, ramp, or damped sinusoidal waveform which is most efficient with respect to the transmembrane potential response within the myocardium is delivered by using an amplifier array where any two, three, or four amplifiers and their respective electrodes may be driven differentially as to draw current through selected current pathways or different angular perspectives. Also, any one amplifier may be driven differentially to any of the other three amplifiers simultaneously using the same arbitrary waveform or any one amplifier may be driven differentially to any of the other three amplifiers sequentially using individual arbitrary waveforms at different or equal voltage and current amplitudes. With use of this approach, many combinations of shock deliveries are possible and can be selected by the electrophysiologist based on individual patient requirements for cardioversion or defibrillation.

The amplifiers will process any waveform through the atria as directed and programmed by an electrophysiologist such as ascending or descending exponential, square, sine, triangle, ramp, saw tooth, etc. The voltage amplitude range shall optimally be from about 0 to about 200VDC. This system employs two energy sources as directed by the electrophysiologist. The DC/DC converter runs first to charge the shocking capacitors and then may run simultaneously while the shocking capacitors are being discharged. A current limit is employed within the high voltage converter electronics for the purpose of keeping the battery peak currents within normal limits. The peak currents are delivered by the shocking capacitors during that peak current time period as dictated by the waveform chosen by the electrophysiologist.

According to the invention an implantable atrial defibrillation device is provided which uses less energy than conventional defibrillation devices by utilizing sequential or simultaneous shocks at a reduced voltage amplitude thereby reducing pain levels associated with electrical shocks.

It is an aspect of the invention to provide an implantable defibrillator which defibrillates with lower peak voltage and current waveforms which minimize tissue stunning and damage.

In another aspect of the invention an external defibrillator device is provided which defibrillates with a higher voltage and current using the same circuit topologies and principles as the implantable version. The goal is to reduce the overall pain level using the arbitrary waveforms specified herein.

Another aspect of the invention is directed to defibrillation using biphasic sequential shocking pulses that are in the range of from about 2.5 ms to about 8 ms, optionally from about 3 ms to about 6 ms, positive and negative time periods to minimize energy consumption.

In an embodiment of the invention, a method for treating atrial fibrillation or atrial tachycardia comprises dynamically steering or selecting two or more current vector paths sequentially or simultaneously for defibrillation to change the transmembrane potential in the left and right atria sufficiently to halt AF or AT.

In another embodiment of a method of the invention, there are smaller shocks than required using traditional devices which defibrillate through a single current path or using devices that deliver shocks across two or more current pathways but that cannot dynamically alter or steer the voltage and current amplitude through each pathway.

In another embodiment of the invention, the method or apparatus is designed to treat atrial tachycardias, including but not limited to, atrial tachycardia, atrial flutter, both typical and atypical, and atrial fibrillation.

In another embodiment of a method of the invention, the method comprises delivering biphasic ascending or descending exponential, ramp, or damped sinusoidal waveforms which are most efficient with respect to the transmembrane potential response within the myocardium by use of an amplifier array where any two, three, or four amplifiers and their respective electrodes may be driven differentially as to draw current through selected current pathways or different angular perspectives within the right and left atria to rapidly terminate AF and AT.

In another embodiment of a method or apparatus of the invention, any one amplifier may be driven differentially to any of the other three amplifiers simultaneously using the same arbitrary waveform, or any one amplifier may be driven differentially to any of the other three amplifiers sequentially using individual arbitrary waveforms at different or equal voltage and current amplitudes.

In another embodiment of a method or apparatus of the invention, arbitrary waveforms can be delivered to multiple electrode configurations and employing multiple sequential or simultaneous shocking paths.

In another embodiment of a method or apparatus of the invention, amplifiers process any waveform through the atria as directed by an electrophysiologist such as ascending or descending exponential, square, sine, triangle, ramp, saw tooth, etc.

In another embodiment of a method or apparatus of the invention, the voltage amplitude shall be from about 0 to about 200VDC.

In another embodiment of a method or apparatus of the invention, a combination of direct delivery converter energy and sequentially or simultaneous timed capacitive discharges make up the total energy that is processed through the amplifiers for defibrillation or cardioversion.

In another embodiment of a method or apparatus of the invention, an implantable atrial defibrillation and/or atrial tachycardia cardioversion device uses less energy than conventional defibrillation devices, thereby reducing pain levels, tissue stunning, and damage associated with very high voltage electrical shocks.

In another embodiment of a method or apparatus of the invention, transmembrane potentials are achieved using lower leading edge peak voltages and sequential or simultaneous arbitrary waveform shocks.

In another embodiment of a method or apparatus of the invention, two capacitors are discharged that will deliver sequential or simultaneous biphasic waveforms at any time interval during each shock cycle as to deliver the majority of the shock energy through the amplifiers at the time period where the peak current is at the highest level with respect to the selected waveform and battery drain.

In another embodiment of a method or apparatus of the invention, timed capacitor shock deliveries will minimize battery drain while the amplifier delivers the desired waveform as programmed by an electrophysiologist.

In another embodiment of a method or apparatus of the invention, the medical criteria include, but are not limited to, gender, size, weight, age, and degree or type of heart disease.

In another embodiment of a method or apparatus of the invention, individual requirements are selected from the software protocol based upon various medical criteria as defined by the electrophysiologist.

In another embodiment of a method or apparatus of the invention, biphasic sequential or simultaneous shocking pulses that are in the about 2.5 ms to about 8 ms positive and negative time periods, respectively, are used to defibrillate, to minimize energy consumption and to conserve battery life.

In another embodiment of the invention, an apparatus for treating atrial fibrillation or atrial tachycardia comprises means for dynamically steering or selecting two or more current vector paths sequentially or simultaneously for defibrillation to change the transmembrane potential in the left and right atria sufficiently to halt AF or AT.

In another embodiment of a method or apparatus of the invention, smaller shocks than required using traditional devices which defibrillate through a single current path or using devices that deliver shocks across two or more current pathways but that cannot dynamically alter or steer the voltage and current amplitude through each pathway.

In another embodiment of the invention, an apparatus is designed to treat atrial tachycardias, including but not limited to, atrial tachycardia, atrial flutter, both typical and atypical, and atrial fibrillation.

In another embodiment of the invention, an apparatus for treating atrial fibrillation or atrial tachycardia comprises means for delivering biphasic ascending or descending exponential, ramp, or damped sinusoidal waveforms which are most efficient with respect to the transmembrane potential response within the myocardium by use of an amplifier array where any two, three, or four amplifiers and their respective electrodes may be driven differentially as to draw current through selected current pathways or different angular perspectives within the right and left atria to rapidly terminate AF and AT.

In another embodiment of an apparatus of the invention, any one amplifier may be driven differentially to any of the other three amplifiers simultaneously using the same arbitrary waveform, or any one amplifier may be driven differentially to any of the other three amplifiers sequentially using individual arbitrary waveforms at different or equal voltage and current amplitudes.

BRIEF DESCRIPTION OF THE DRAWINGS

FIGS. 4 and 4A each depict ascending or descending exponential, ramp, and damped sinusoidal waveforms with the time periods identified with respect to converter run time and capacitor discharge timing.

DETAILED DESCRIPTION OF THE DRAWINGS

Figure 1:
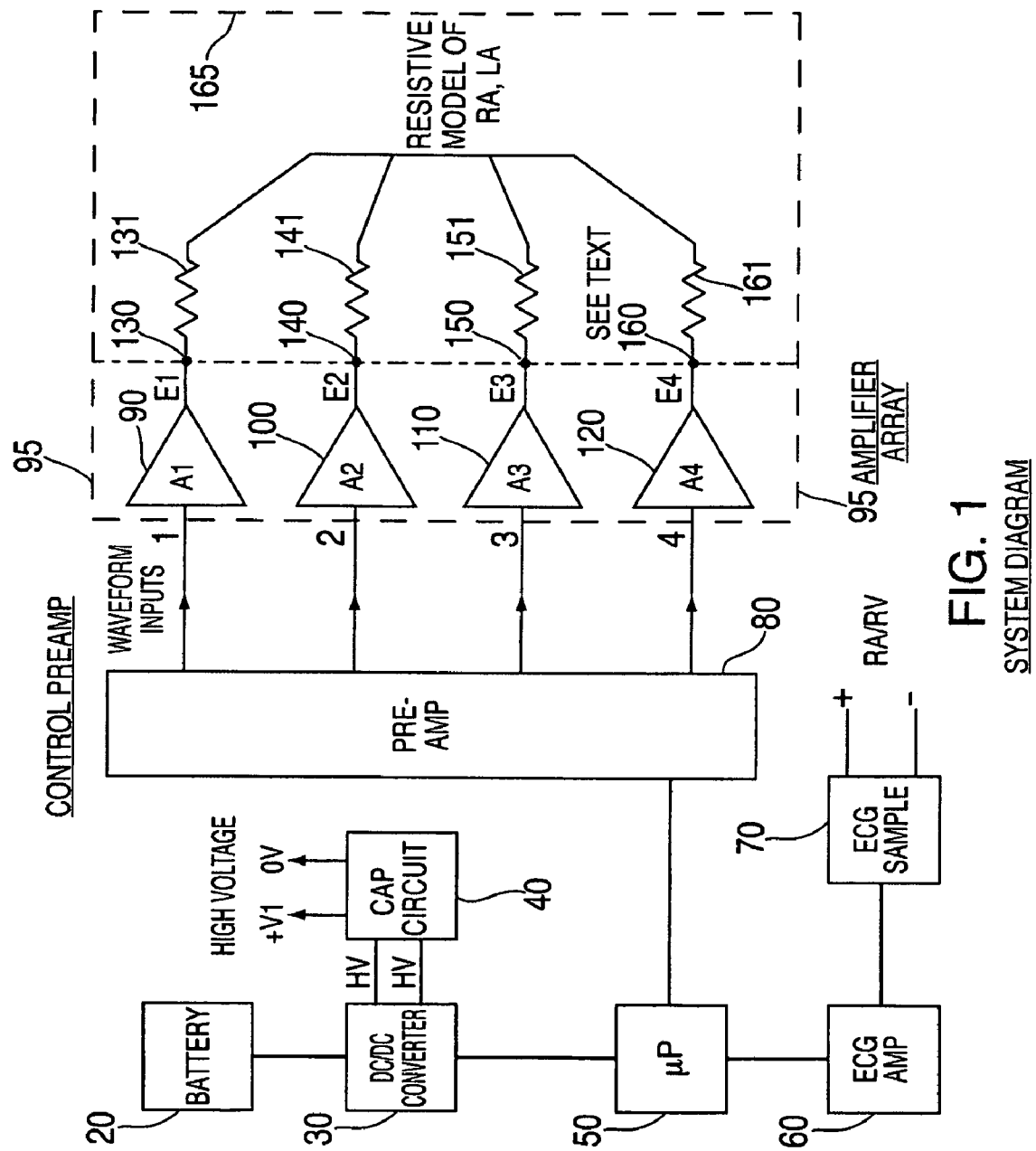
FIG. 1 depicts a system overview of an implantable atrial defibrillation device and its major components and circuit architecture.

FIG. 1 illustrates the defibrillation system according to the present invention. The battery 20 provides power to the pulse width modulated [PWM] and regulated DC/DC converter 30 which in turn distributes a control voltage to the microprocessor 50, the ECG Amp 60 and the ECG Sense Analyzer 70 as well as the control preamp 80. The DC/DC 30 converter also distributes high voltage to the capacitor circuit 40 and the four amplifiers 90, 100, 110, and 120. The PWM regulated DC/DC converter shall have a dynamic, programmable current limit circuit as part of the overall converter design. Electrodes E1, E2, E3, and E4 130, 140, 150, and 160 with their respective wires are installed electrodes that are placed chronically in the SVC, right atria, coronary sinus and coronary veins that are on the left side of the heart. These structures are entered from the SVC and then through the right atrium as specified by the electro-physiologist cardiologist. Also illustrated are heart muscle resistances 165 depicted by 131, 141, 151, and 161. These resistances represent the effective defibrillation load in which the voltage and current from the amplifiers deliver defibrillation shocks between any two, three, or four amplifiers sequentially or simultaneously.

Figure 2:
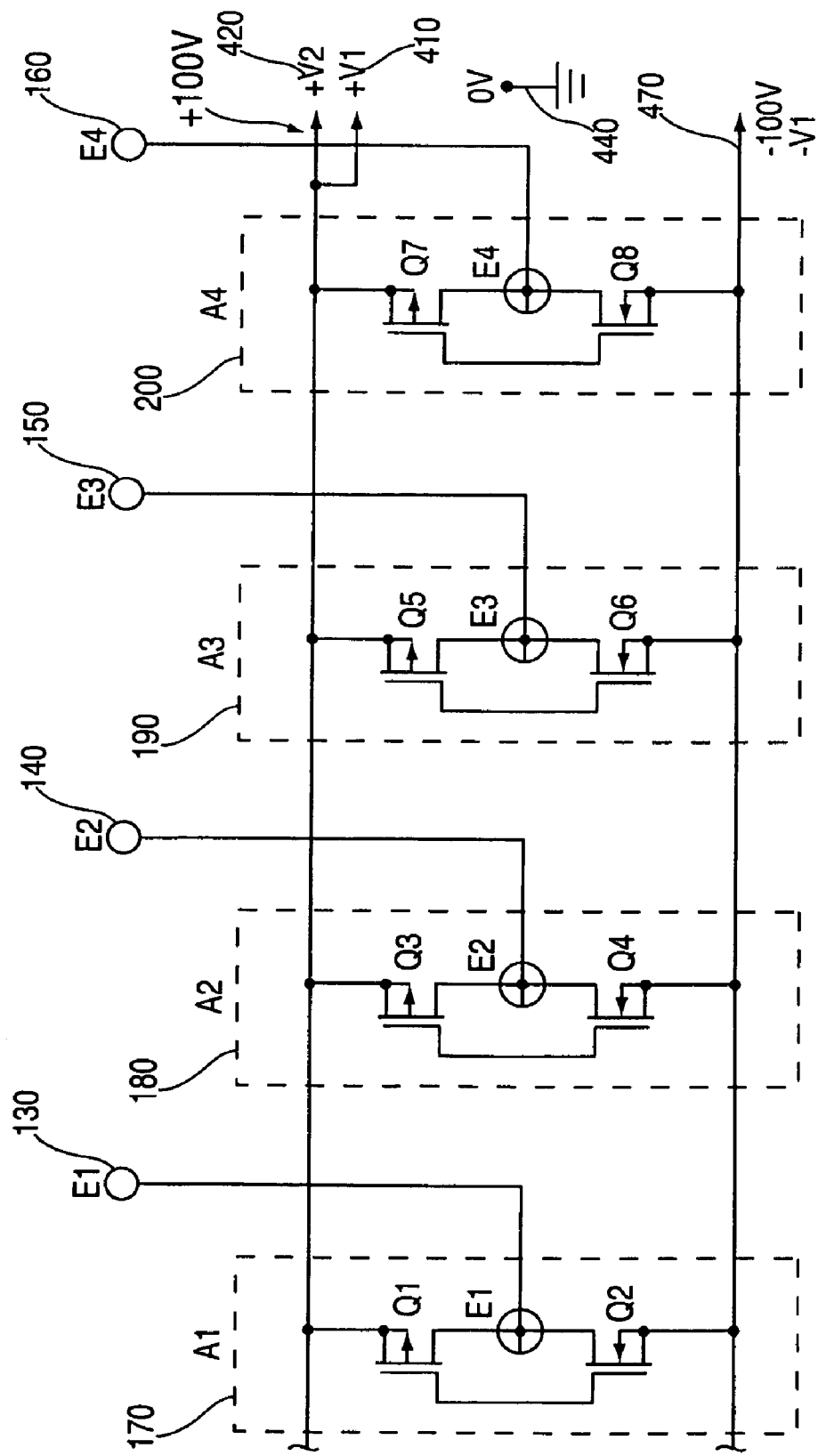
FIG. 2 depicts an amplifier array in which any two, three, or four amplifiers can be driven differentially as to dynamically select current vectors and pathways.

FIG. 2 illustrates the array which is made up by four individual amplifiers A1-170, A2-180, A3-190, and A4-200 with a limited bandwidth of DC to 500 Hz. The bandwidth is designed to deliver rapid defibrillation pulses yet be immune to high frequency noise or interference with other electronic devices. A ground return 440 is shown which represents zero volts. Each amplifier can be differentially driven as in a bridge configuration for current vector selection. MOSFETS are depicted as amplifier output power devices; however, IGBTs, bipolar transistors, or any other suitable semiconductor devices may be employed as well to meet the design criteria for the present invention by those skilled in the art of power circuit designs. Power supply voltages of +100V 420 and −100V 470 are available for each half cycle of the shocking waveform which represents 200V peak to peak for positive and negative shock pulses. This system dynamically steers or selects different current vectors and different angular delivery perspectives sequentially or simultaneously as to reduce the total energy requirements for atrial defibrillation and to terminate atrial tachycardia.

Figure 3:
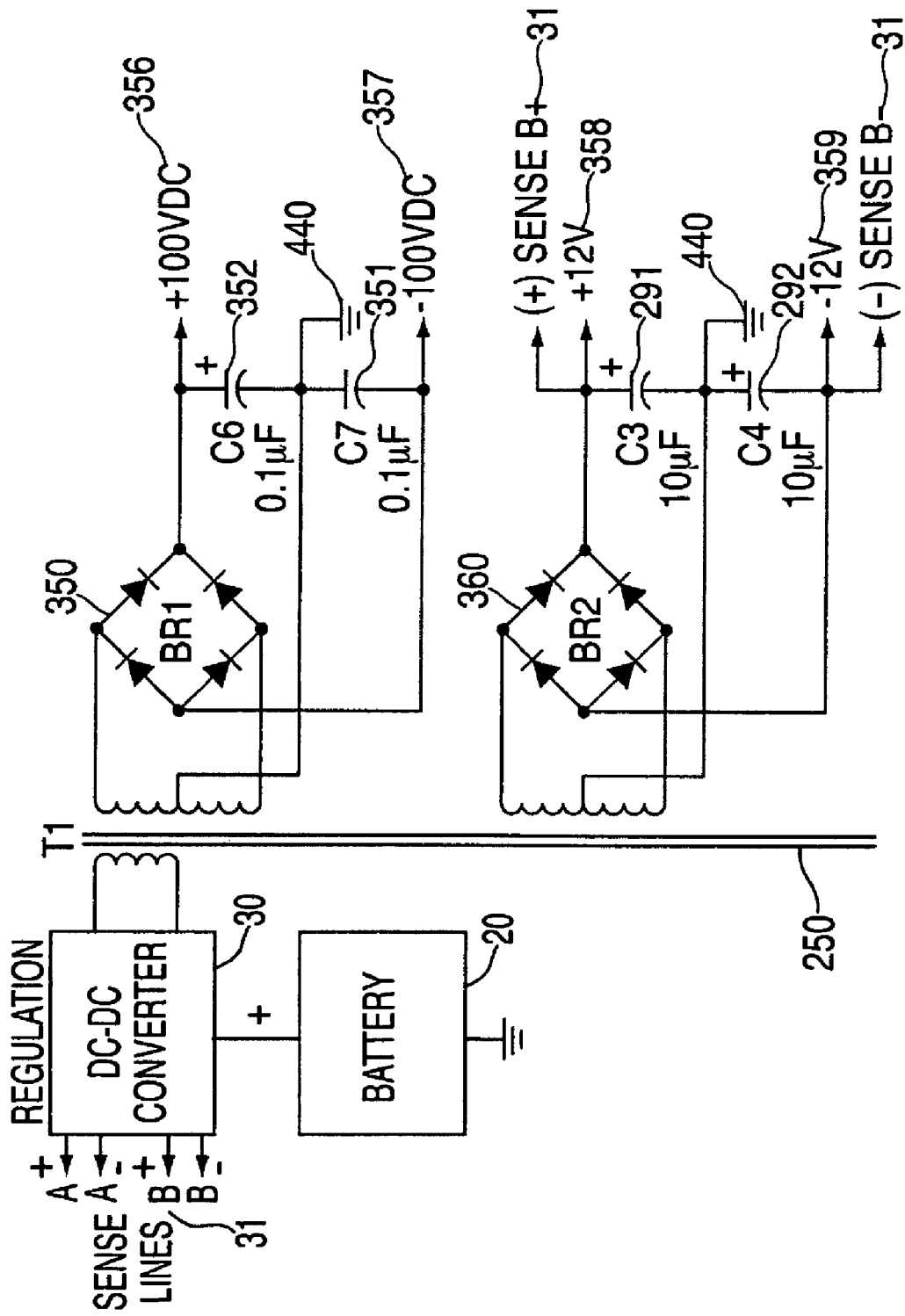
FIGS. 3 and 3A depict the DC/DC converter associated with its secondary power supplies for delivery of low voltage to control circuits and high voltage to the amplifier array. Note the capacitor circuit for increased current capability during peak current conditions.
Figure 3A:
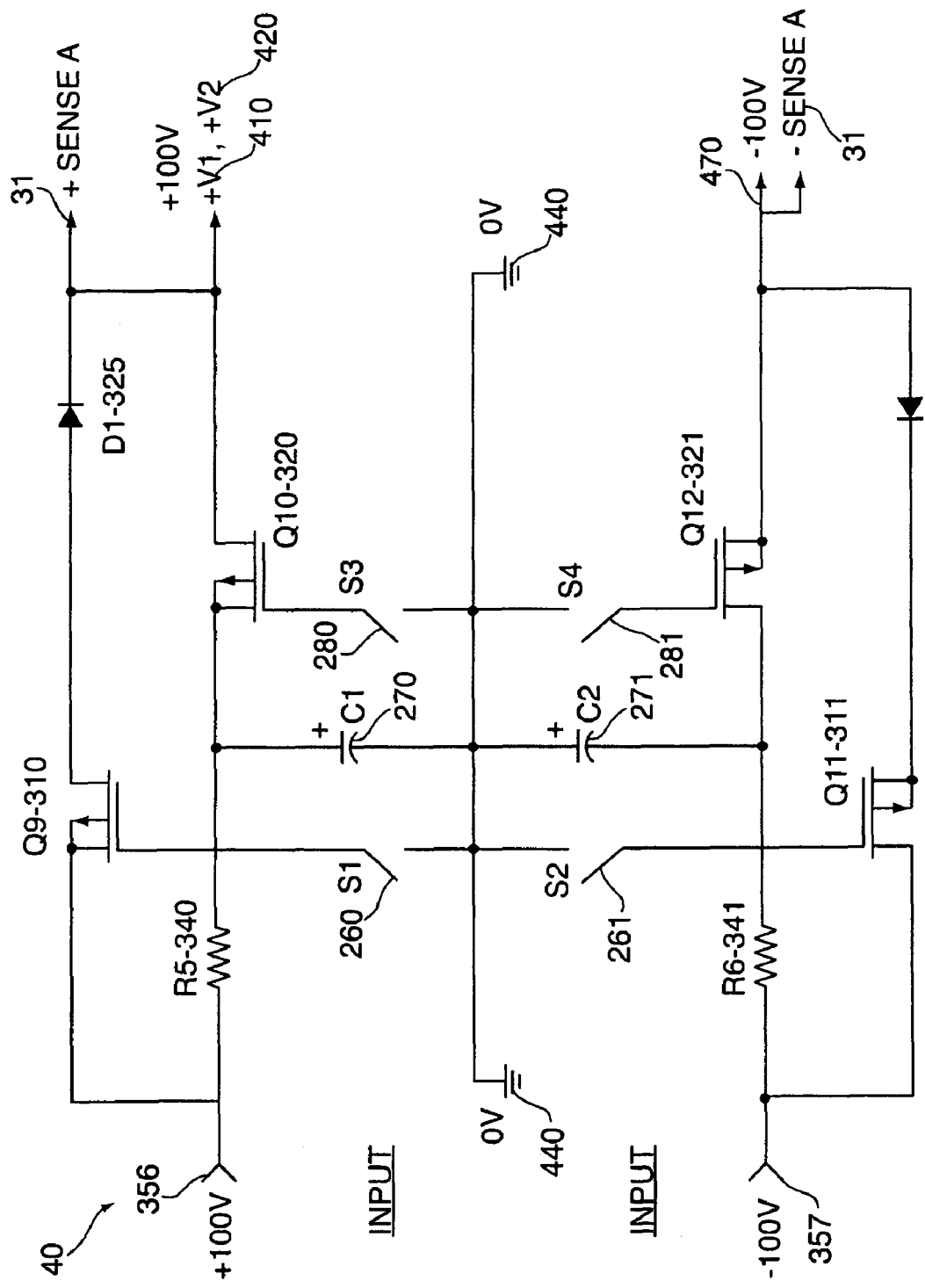

FIGS. 3 and 3A illustrate the design architecture for the power supplies used in the present invention. A PWM regulated DC/DC converter 30 is powered by the battery 20 which converts a low voltage from the battery 20 to a higher voltage output via switching circuitry within the DC/DC converter 30 and is delivered through the transformer T1-250 for isolation from primary to secondary. Voltage regulation is achieved via the sense 31 or feedback lines. T1-250 delivers voltage and current to BR2-360 which convert the alternating current and voltage from T1-250 into a DC voltage and current which is then filtered using C3-291 and C4-292 and delivered to the control electronics in FIG. 1 as +12VDC-358 and −12VDC-359. T1-250, in a similar fashion BR1-350 and filter capacitors C6-352 and C7-351 deliver high DC voltages and current to the amplifier rails A1-170, A2-180, A3-190, and A4-200. This is a high voltage circuit 420 which supplies voltage and current to the amplifiers during the entire pulse duration as commanded by the microprocessor 50 and is current limited. A ground return 440 is shown which represents zero volts. R5-340, C1-270 and R6-341, C2-271 form capacitor charging circuits which charge over a brief time period of approximately 2-3 seconds prior to the sequential pulse deliveries. C1-270, C2-271 can be discharged onto the high voltage rails at any time during the delivery of the shocking waveform. The value of C1-270 and C2-271 will be approximately 22-100 uF rated at 200WVDC. Transistor Q9-310 and Q11-311 are commanded by the microprocessors S1-260 and S2-261 as MOSFET switches or similar to allow the converter to deliver voltage and current on command. The charges for C1-270 and C2-271 are delivered through R5-340 and R6-341 via T=RC×5 time constants to achieve a 99% voltage charge. Q10-320 and Q12-321 are commanded by the microprocessors S3-280 and S4-281 as MOSFET switches or similar to apply the energy stored in C1-270 and C2-271 onto the amplifier array 95 rails at anytime during the shocking waveform. The timing of the energy delivery from C1-270 and C2-271 depends on the type of waveform selected. If the electrophysiologist selects an ascending exponential waveform, the capacitors C1-270 and C2-271 will be discharged sequentially or simultaneously at the end of the defibrillation cycle where the peak current occurs. If the electrophysiologist selects a square waveform, the capacitors C1-270 and C2-271 will be discharged sequentially or simultaneously at the beginning of the defibrillation cycle where the peak current occurs. D1-325 and D2-327 rectifier diodes are in series with the high voltage output of the converter 30 for the purpose of gating the voltage and current as to not interfere with the capacitor discharge circuit. Any combination of biphasic waveform pulses and amplitudes may be selected and programmed such as a positive pulse being an exponential ascending or descending waveform and the negative waveform may be programmed to be a square wave or a truncated exponential waveform with descending tilt that comprises a biphasic pulse.

Figure 4:
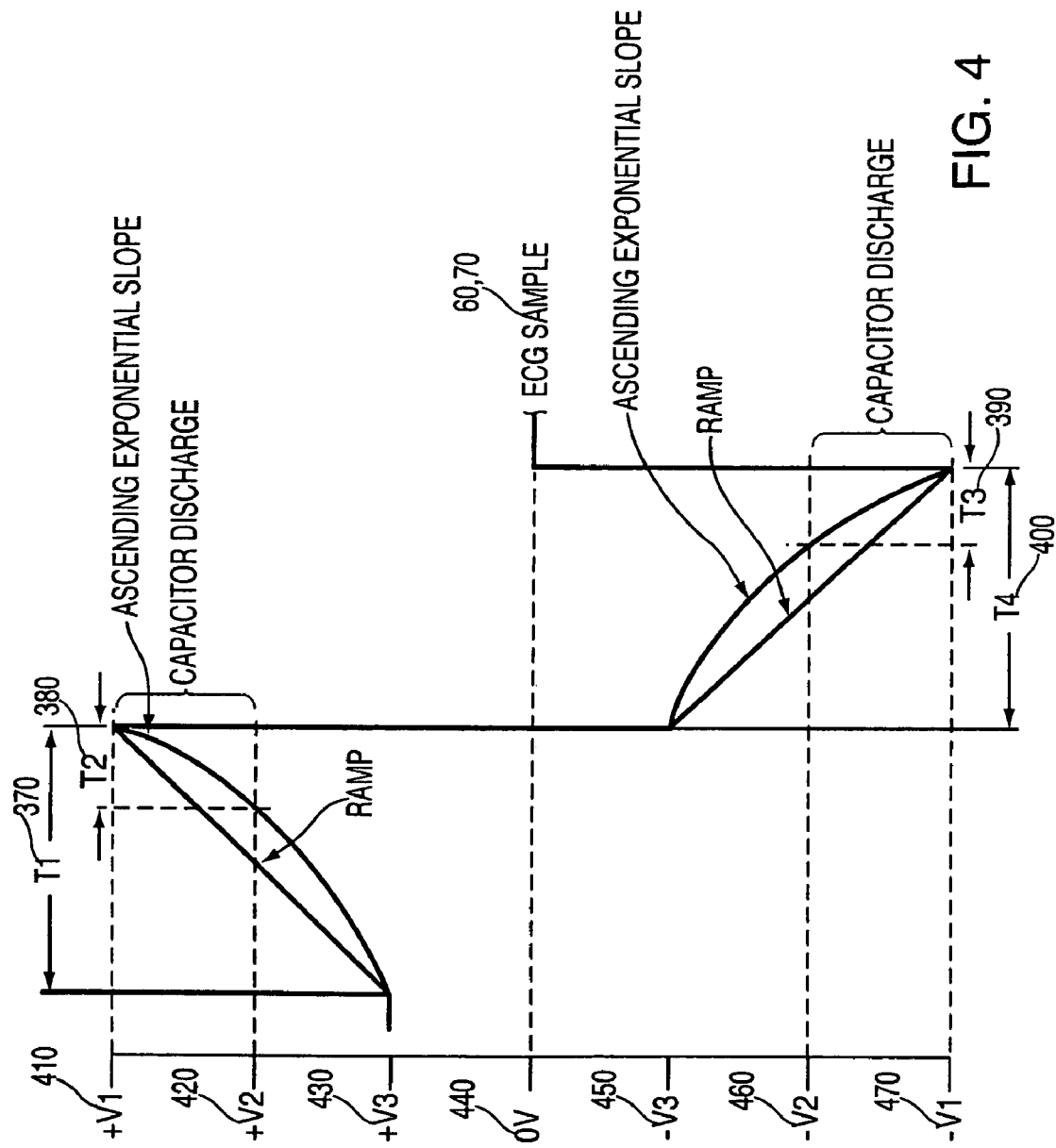

FIGS. 4 and 4A illustrate exemplary ascending or descending exponential, ramp, or damped sinusoidal waveforms with timing and amplitude points of interest. Positive voltage levels of interest are depicted as +V1-410, +V2-420, and +V3-430 as well as negative voltage levels −V1-470, −V2-460, and −V3-450. The positive or negative V3 voltage threshold may be started at any value from zero to 100 volts with 25-75 volts being the most efficient starting point for a shock. Starting V3 at zero wastes time and energy especially for the ascending exponential or ramp waveforms. The 0V ground return 440 is at a zero state and is a reference for the other voltage potentials. The intersections of T2-380 and +V2 as well as T3-390 and −V2 depict the time interval where capacitors C1-270 and C2-271 are discharged onto the amplifier rails 420 and 470. Time periods T1-370 and T4-400 represent the total time duration of the positive and negative pulse durations. ECG sense amp and analyze 60 and 70 occur between defibrillation shock intervals to check the progress of the atrial fibrillation or atrial tachycardia conversion. This system employs two energy sources as directed by the electrophysiologist. The DC/DC converter runs first to charge the shocking capacitors C1-270 and C2-271 and then may run simultaneously while the shocking capacitors C1-270 and C2-271 are being discharged. A current limit is employed within the high voltage DC/DC converter electronics 30 for the purpose of keeping the battery 20 peak currents within normal limits. The voltage and current are delivered by the shocking capacitors C1-270 and C2-271 during that peak current time period as dictated by the waveform chosen by the electrophysiologist. The converter 30, voltage and current provide the basis for the basic waveform being amplified and at a programmed time during the shocking pulse, the capacitors C1-270 and C2-271 are discharged to deliver the peak energy as required. Conversely, capacitors C1-270 and C2-271 may be applied to the rails after they are fully charged to deliver the shocking voltage and current through the amplifier array while the converter is off.

Figure 5:
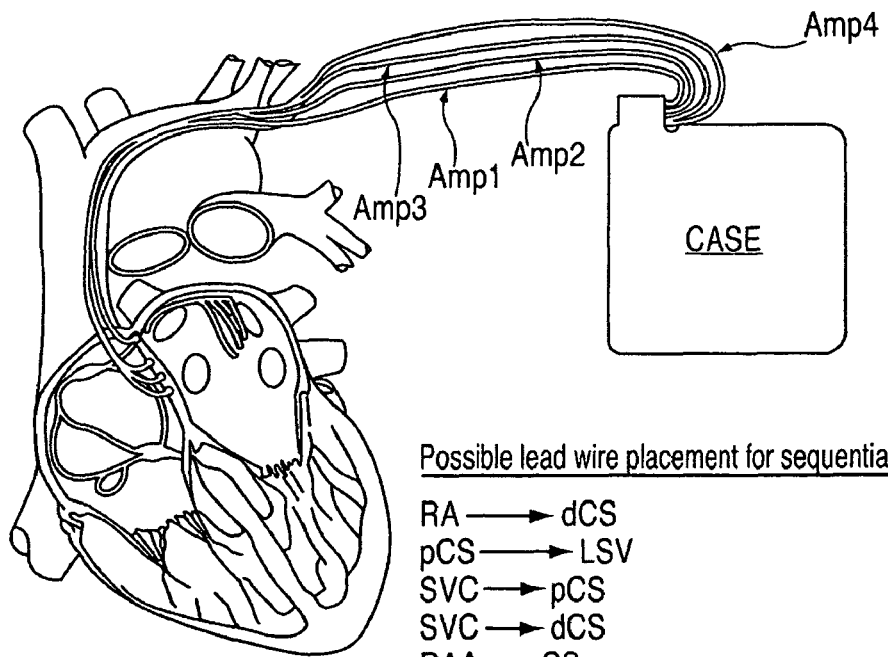
FIG. 5 depicts the right and left atria of the heart where an electrophysiologist will select and install electrodes that are placed chronically in the coronary sinus and coronary veins that are on the left side of the heart as well as selected positions within the right atria. These structures are entered from the superior vena cava [SVC] and then through the right atria.

FIG. 5 illustrates possible wire and electrode placement and locations that an electrophysiologist cardiologist skilled in the art of arrhythmia management may choose for successful defibrillation or cardioversion using sequential shocks for atrial fibrillation, atrial flutter and or atrial tachycardia. By applying different voltage amplitudes, pulse widths and pulse shapes through the atria via the electrodes provided, the voltage and current may be dynamically steered to achieve the desired results for defibrillation or cardioversion.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A method for treating atrial fibrillation or atrial tachycardia in a patient, which comprises sequentially or simultaneously delivering to the patient's heart through at least two leads or electrodes signals having arbitrary waveforms for defibrillation, wherein the amplitude of voltage and/or current for each lead or electrode is varied by using an amplifier array to change the transmembrane potential in the left and right atria in the patient's heart sufficiently to halt AF or AT.

2. The method of claim 1, wherein the amplifier array delivers biphasic arbitrary waveform defibrillation shocks across one or more current pathways through the patient's heart.

3. The method of claim 1, wherein an ICD delivers cardioversion and/or defibrillation arbitrary shocking waveforms.

4. The method of claim 1, wherein an implantable atrial defibrillation and/or atrial tachycardia cardioversion device uses less energy than conventional defibrillation devices, thereby reducing pain levels, tissue stunning, and damage associated with very high voltage electrical shocks.

5. The method of claim 4, wherein transmembrane potentials are achieved using lower leading edge peak voltages and sequential or simultaneous arbitrary waveform shocks.

6. The method of claim 5, wherein unique electrical shock techniques are employed to match the transmembrane potentials and RC time constants within the myocardium using specialized electronic power amplifier designs and software commands to deliver arbitrary waveform defibrillation and cardioversion shocking pulses through the myocardium.

7. The method of claim 1, wherein two capacitors are discharged that will deliver sequential or simultaneous biphasic waveforms at any time interval during each shock cycle as to deliver the majority of the shock energy through the amplifiers at the time period where the peak current is at the highest level with respect to the selected waveform and battery drain.

8. The method of claim 7, wherein timed capacitor shock deliveries will minimize battery drain while the amplifier delivers the desired waveform as programmed by an electrophysiologist.

9. The method of claim 1, wherein biphasic sequential or simultaneous shocking pulses that are in the about 2.5 ms to about 8 ms positive and negative time periods, respectively, are used to defibrillate, to minimize energy consumption and to conserve battery life.

10. The method of claim 9, wherein many combinations of defibrillation or cardioversion shocks are available for selection and delivered via a single shock protocol using arbitrary waveforms.

11. The method of claim 1, wherein an electrophysiologist can select pre-programmed and pre-defined software waveform protocols, wherein many combinations of shock deliveries are possible based on individual patient requirements for cardioversion or defibrillation.

12. The method of claim 11, wherein the individual requirements are selected from the software protocol group based upon various medical criteria as defined by the electrophysiologist.

13. The method of claim 1 which is accomplished by using unique arbitrary waveform shocks.

14. The method of claim 1, wherein the AT is automatic, triggered, or reentrant.

15. A method for treating atrial fibrillation or atrial tachycardia in a patient, which comprises delivering biphasic ascending or descending exponential, ramp, or damped sinusoidal waveforms which are compatible with the transmembrane potential response within the myocardium by use of an amplifier array where any two, three, or four amplifiers and their respective electrodes may be driven differentially as to draw current through selected current pathways or different angular perspectives within the right and left atria to rapidly terminate AF or AT.

16. The method of claim 15, wherein any one amplifier may be driven differentially to any of the other three amplifiers simultaneously using the same arbitrary waveform, or any one amplifier may be driven differentially to any of the other three amplifiers sequentially using individual arbitrary waveforms at different or equal voltage and current amplitudes.

17. The method of claim 15, wherein arbitrary waveforms can be delivered to multiple electrode configurations and employing multiple sequential or simultaneous shocking paths.

18. The method of claim 17, wherein a waveform is ascending or descending exponential, ramp, damped sine, square, sine, triangle, or saw tooth or any geometric shape which an amplifier can process.

19. The method of claim 17, wherein the amplifiers will process any waveform through the atria as directed by an electrophysiologist.

20. The method of claim 17, wherein the voltage amplitude shall be from about 0 to about 200VDC.

21. The method of claim 15, wherein a combination of direct delivery converter energy and sequentially or simultaneously timed capacitive discharges make up the total energy that is processed through the amplifiers for defibrillation or cardioversion.

22. An apparatus for treating atrial fibrillation or atrial tachycardia, which comprises
means for sequentially or simultaneously delivering to the patient's heart through at least two leads or electrodes signals having arbitrary waveforms for defibrillation; and
an amplifier array,
wherein the amplitude of voltage and/or current for each lead or electrode is varied by using the amplifier array to change the transmembrane potential in the left and right atria sufficiently to halt AF or AT.

23. The apparatus of claim 22, wherein the amplifier array delivers biphasic arbitrary waveform defibrillation shocks across one or more current pathways through the patient's heart.

24. An apparatus of claim 22 which is designed to treat atrial fibrillation and atrial tachycardia.

25. An apparatus for treating atrial fibrillation or atrial tachycardia in a patient, which comprises means for delivering biphasic ascending or descending exponential, ramp, or damped sinusoidal waveforms which are compatible with the transmembrane potential response within the myocardium by use of an amplifier array where any two, three, or four amplifiers and their respective electrodes may be driven differentially to draw current through selected current pathways or different angular perspectives within the right and left atria to rapidly terminate AF or AT.

26. The apparatus of claim 25, wherein any one amplifier may be driven differentially to any of the other amplifiers simultaneously using the same arbitrary waveform, or any one amplifier may be driven differentially to any of the other amplifiers sequentially using individual arbitrary waveforms at different or equal voltage and current amplitudes.

* * * * *